(12) United States Patent
Burns, Jr. et al.

(10) Patent No.: US 8,915,832 B2
(45) Date of Patent: Dec. 23, 2014

(54) METHOD FOR BIFOLDING AN ARTICLE AND ARTICLE MADE THEREBY

(75) Inventors: John Glasgow Burns, Jr., Cincinnati, OH (US); Yoichiro Yamamoto, Cologne (DE)

(73) Assignee: The Procter & Gamble Company, Cincinnati, OH (US)

( * ) Notice: Subject to any disclaimer, the term of this patent is extended or adjusted under 35 U.S.C. 154(b) by 1095 days.

(21) Appl. No.: 12/910,986

(22) Filed: Oct. 25, 2010

(65) Prior Publication Data

US 2011/0039678 A1 Feb. 17, 2011

Related U.S. Application Data

(62) Division of application No. 12/203,336, filed on Sep. 3, 2008, now Pat. No. 7,846,082.

(60) Provisional application No. 60/967,896, filed on Sep. 7, 2007.

(51) Int. Cl.
*B31F 1/08* (2006.01)

(52) U.S. Cl.
USPC ............................ 493/424; 493/418; 493/450

(58) Field of Classification Search
USPC ......... 493/424, 418, 450, 356, 231, 432, 428, 493/441, 423
See application file for complete search history.

(56) References Cited

U.S. PATENT DOCUMENTS

| | | | |
|---|---|---|---|
| 4,521,209 A | 6/1985 | DuFresne | |
| 5,031,891 A | 7/1991 | Kobler et al. | |
| 5,904,802 A | 5/1999 | Niedermeyer | |
| 6,120,487 A | 9/2000 | Ashton | |
| 6,513,221 B2 | 2/2003 | Vogt et al. | |
| 6,900,450 B2 | 5/2005 | Gimenez et al. | |
| 7,399,266 B2 | 7/2008 | Aiolfi et al. | |
| 2002/0174930 A1 | 11/2002 | Umebayashi et al. | |
| 2006/0276320 A1 | 12/2006 | Aiolfi et al. | |
| 2009/0094941 A1 | 4/2009 | Burns et al. | |
| 2009/0098995 A1 | 4/2009 | Burns et al. | |

FOREIGN PATENT DOCUMENTS

| | | |
|---|---|---|
| WO | WO 97/34556 A | 9/1997 |
| WO | WO 00/35776 A | 6/2000 |

OTHER PUBLICATIONS

International Search Report, Nov. 21, 2008, 5 pages.

*Primary Examiner* — Sameh H. Tawfik
(74) *Attorney, Agent, or Firm* — John G. Powell; Amy M. Foust

(57) ABSTRACT

A method is provided for bifolding articles on a high speed production line on which the articles are moved along a predetermined path. The method includes the use of a vacuum conveyor assembly to engage the leading end portion of an article and transport it in the machine direction, thereby potentially reducing the occurrence of undesirable misalignment of the article end edges during a bifolding process.

18 Claims, 10 Drawing Sheets

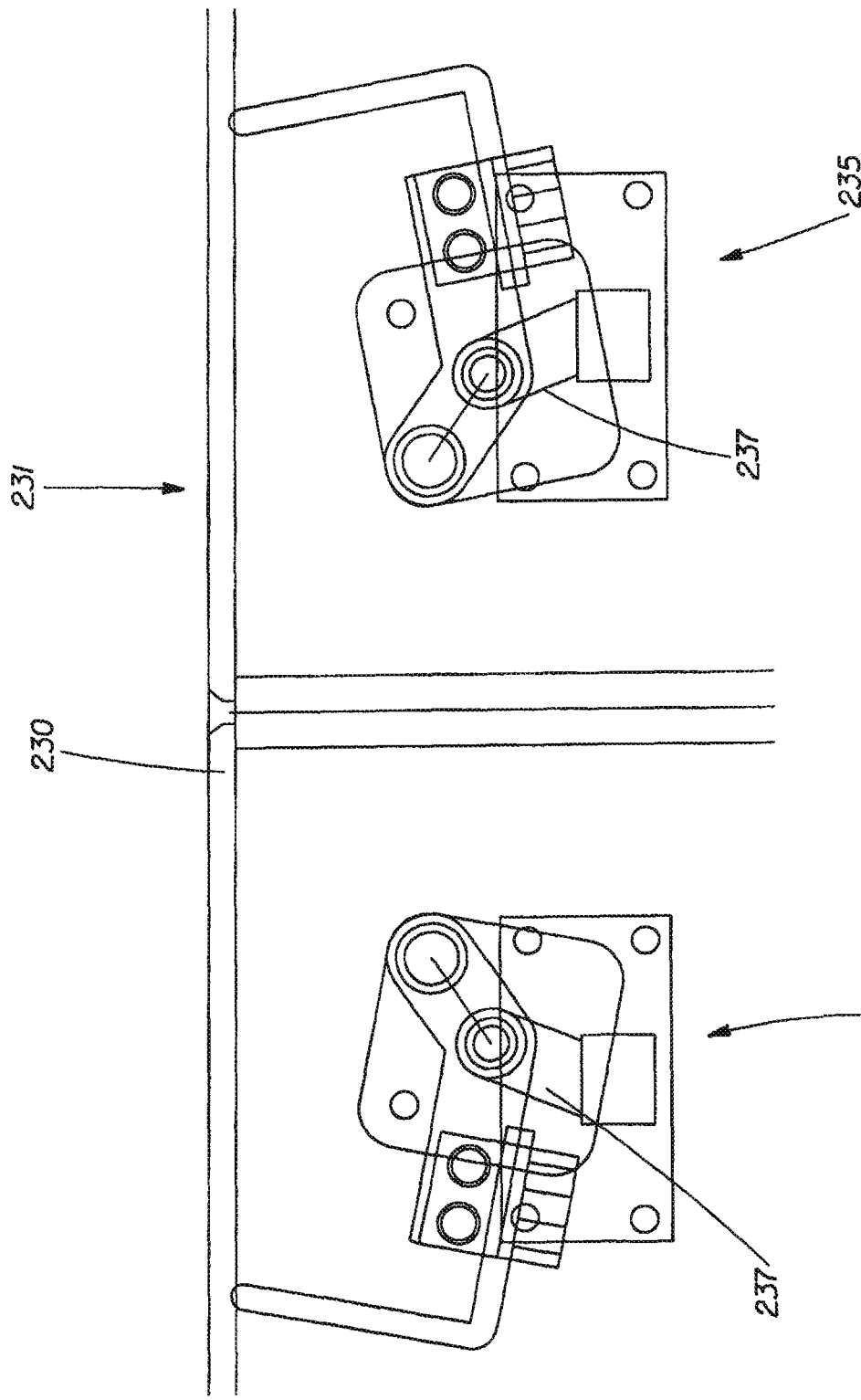

METHOD FOR BIFOLDING AN ARTICLE AND ARTICLE MADE THEREBY

CROSS REFERENCE TO RELATED APPLICATIONS

This application is a divisional application of U.S. Ser. No. 12/203,336, now U.S. Pat. No. 7,846,082 which claims the benefit of U.S. Provisional Application No. 60/967,896, filed Sep. 7, 2007.

FIELD OF THE INVENTION

Disclosed is a method for bifolding articles and the articles made thereby. More particularly, disclosed is a method for bifolding disposable absorbent articles such as diapers, training pants, and incontinence pads and bifolded articles having substantially aligned end edges.

BACKGROUND OF THE INVENTION

Disposable absorbent articles, such as diapers, pull-on diapers, training pants, adult incontinence pads, wipes, facial tissue, toilet tissue, napkins, paper towels and the like are often manufactured and/or packaged on a high-speed production line where individual articles may move along a production path at a speed of hundreds of meters per minute. During the manufacturing and/or packaging process it is not uncommon for the disposable absorbent article to undergo a folding process. For example, a disposable diaper may undergo a bifolding process prior to being placed in a package. In a bifolding process, an article is folded into two parts. The article may be folded in half in the longitudinal direction such that two opposing portions of the article are brought together in a face-to-face configuration. At least some manufacturers of disposable diapers desire to provide a bifolded diaper that has a front end edge that is substantially aligned with a back end edge of the diaper. However, current manufacturing practices often do not provide the desired degree of alignment between the diaper end edges, resulting in a diaper that may have undesirable characteristics in the marketplace. The problem may be further compounded for so-called "training pant" diapers which, after being folded into a U in the same or similar way as conventional diapers, are joined permanently, e.g., sealed, along the lateral portions to form a closed annular girdle enabling the diaper to be used pant-fashion. The high degree of precision for folding training pants may require increased accuracy beyond that of a traditional diaper, so that the lateral portions of the training pant, which are to be joined permanently, are configured with the desired overlap.

In one method for providing a folded absorbent article, a portion of a production line for making absorbent articles may include a primary roll for carrying the absorbent article. The primary roll typically uses suction force, e.g. vacuum, to hold the absorbent article in the proper position during the folding process. The process may also include one or more secondary rolls for pulling a portion of the absorbent article, typically the leading end portion, off of the primary roll. The secondary roll(s) may employ vacuum pressure to pull the leading portion of the absorbent article off of the first roll and hold the pulled off portion to the secondary roll surface of the second roll. As the manufacturing process or converting operation continues, more of the leading end portion of the article may continue to be pulled off of the primary roll and attached to the secondary roll. Eventually, the article may be subjected to forces that pull the leading and trailing portions of the article in substantially opposite directions. In some instances, clips or other mechanical holding means may be used to hold the middle portion of the absorbent article to the surface of the primary roll in order to provide sufficient force to pull the leading end portion of the article off of the secondary roll. Typically, once the leading end portion of the article is pulled off of or released by the secondary roll, the leading end portion will travel back toward the primary roll to continue through the folding process. However, when the leading end portion of the article is pulled/released from the secondary roll, it may be subjected to turbulence or other forces that cause it to move about in an uncontrolled manner, potentially resulting in a folded article with undesirably misaligned end and/or side edges.

In order to overcome the problems associated with the uncontrolled movement of the leading end portion when it is separated from the secondary roll, some manufacturers may add a transfer roll or conveyor configured with a vacuum system to receive the leading end portion of the absorbent article and transfer it back to the primary roll. Typically, the surface of the transfer roll or conveyor includes a porous belt or other foraminous surface that allows the suction force of the vacuum system to be exerted at the surface of the conveyor or roll. The surface speed of the transfer conveyor or roll is typically constant, and in some instances is set to match the surface speed of the primary roll. In this way, the leading end portion of the article can be transferred back to the primary roll at about the same speed as the trailing end portion is travelling, potentially reducing the chance for misalignment of the leading and trailing end portions during folding. However, when the leading end portion of the article is separated from the secondary roll, the relative speeds of the leading end portion and the surface of the transfer conveyor or roll may still be substantially different. While the transfer roll or conveyor may be able to capture the leading end portion and hold it to the conveyor or roll surface with vacuum pressure and thereby minimize uncontrolled movement, the leading end portion may still end up in an undesirable configuration (e.g., wrinkled, bunched, crooked, etc.) due to the rapid acceleration typically experienced by the leading edge when it contacts the transfer roll or conveyor.

In addition to the issues related to the different speeds of the transfer conveyor surface and the leading end portion of the article pointed out above, a transfer conveyor or roll may also reduce the speed and/or efficiency at which the manufacturing line can operate. In order to reduce the amount of time it takes to transfer the leading end portion from the peel roll to the transfer conveyor/roll it may be desirable to minimize the distance between the surface of the transfer conveyor/roll and the surface of the secondary roll. However, this typically results in clearances between these two components that only permit one article to be processed at a time. In other words, a second leading end portion cannot be transferred to the secondary roll until the first leading end portion is sufficiently clear of the secondary roll, or the progress of the second leading end portion may be impeded by the presence of the first leading end portion. Further, providing smaller clearances between the surfaces of the various rolls/conveyors may result in reduced manufacturing tolerances and robustness.

In another effort to address the problem of undesirably misaligned end edges, some manufacturers of absorbent articles may include additional material in the end edge portion of the absorbent article so that any misaligned edges can be cut off during the production process. The articles having the cut end edges may appear to be more aligned and still have an end edge of suitable length. But by providing additional material that must be cut off, material and manufacturing costs for producing the absorbent article may increase undesirably. Additionally, other portions of the article may still be noticeably misaligned.

Accordingly, it would be desirable to provide a system for folding articles and providing substantially aligned end and/or side edges on the folded articles. It would also be desirable to provide a system for making such articles without increasing the amount of raw material required to make the absorbent article. It would further be desirable to provide a system for making such articles at an increased manufacturing line speed.

SUMMARY OF THE INVENTION

In order to provide a solution to the problem stated above, at least one embodiment provides a method for folding an article into a bifold configuration. The method comprises placing the article onto a folding drum surface. The article may have a leading end portion and a trailing end portion. The article may be held to the folding drum surface with a holding force. At least a portion of the leading end portion may be transferred to a peel-roll surface, which may be positioned adjacent the folding drum surface. A peel-force may be applied to the leading end portion such that the leading end portion is held to the peel-roll surface by the peel-force. At least a portion of the trailing end portion may be held to the folding drum surface. The leading end portion may be transferred from the peel-roll surface to a movable surface of a vacuum conveyor. The movable surface of the vacuum conveyor may be configured to have a first speed and a second speed. The movable surface of the vacuum conveyor may be driven by a drive mechanism coupled to the movable surface of the vacuum conveyor. The leading end portion may be transferred to the movable surface of the vacuum conveyor when the movable surface of the vacuum conveyor engages the leading end portion at the first speed. The movable surface of the vacuum conveyor may be configured to apply a vacuum force to the leading end portion. The leading end portion may be held to the movable surface of the vacuum conveyor with the vacuum force. The movable surface of the vacuum conveyor may be accelerated to a second speed. The leading end portion may be transferred from the movable surface of the vacuum conveyor to the folding drum such that the leading end and the trailing end are aligned when the article is bifolded.

BRIEF DESCRIPTION OF THE DRAWINGS

FIGS. 2A and 2B are cut-away views of bifold movable clamps of FIG. 2.

DETAILED DESCRIPTION OF THE INVENTION

Definitions

Figure 1:
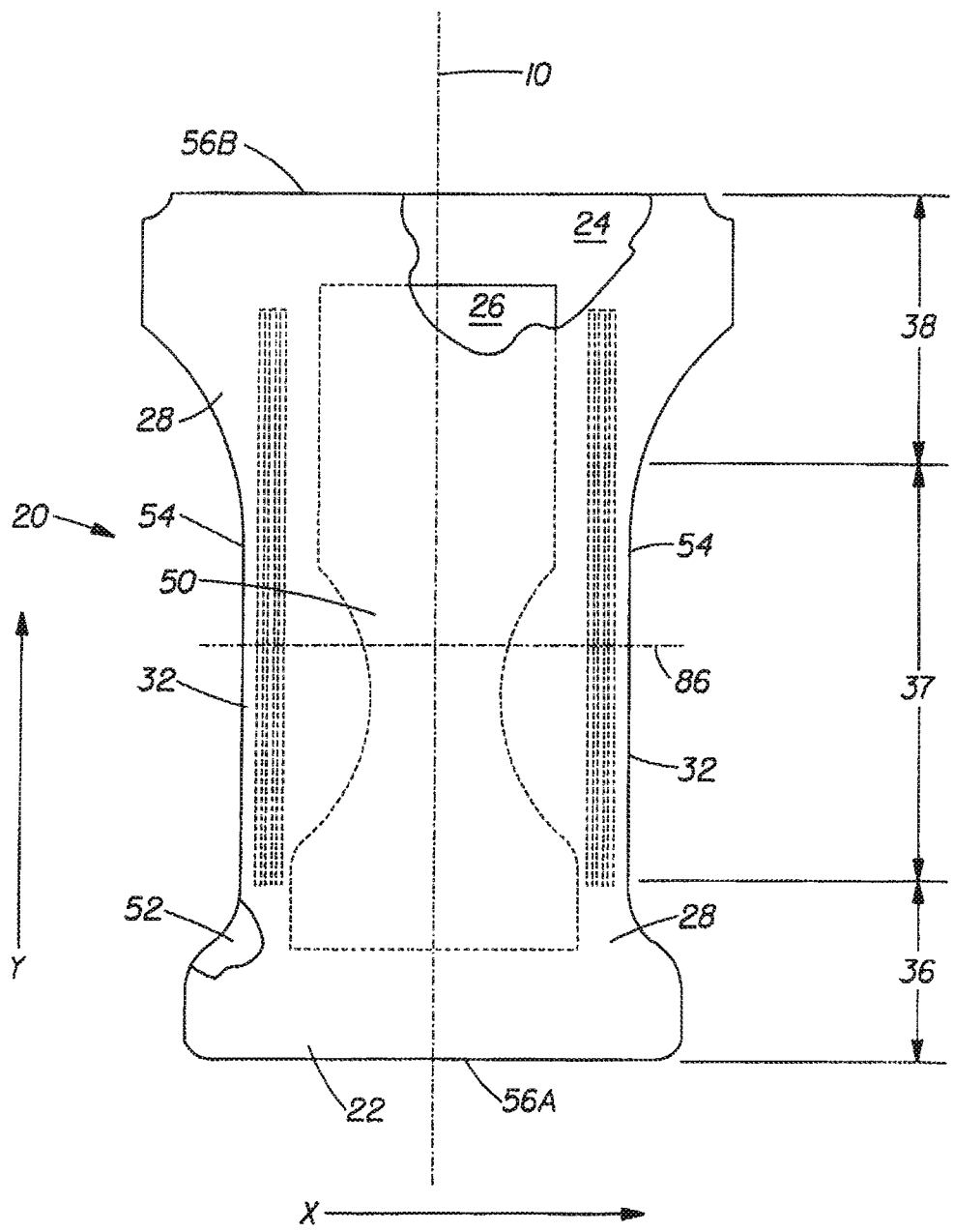
FIG. 1 is a partial cut away view of a diaper in its flat-out, uncontracted state with the body-facing surface oriented toward the viewer.

"Absorbent article" means devices which absorb and contain body exudates and, more specifically, refers to devices which are placed against or in proximity to the body of the wearer to absorb and contain the various exudates discharged from the body. Nonlimiting examples of absorbent articles include diapers, training pants, pull-on pant-type diapers, refastenable diapers or pant-type diapers, incontinence briefs and undergarments, diaper holders and liners, feminine hygiene garments such as panty liners, absorbent inserts, and the like.

"Aligned" means an article in a bifold configuration having an average CD accuracy and an MD accuracy of less than or equal to 3 mm, when measured according to the Alignment Test.

"Bifold" means the leading edge portion and the trailing edge portion of an article on a production line are brought together in a face-to-face configuration along a fold line as the article moves in the machine direction of travel.

"Disposable" means articles that are generally not intended to be laundered or otherwise restored or reused as absorbent articles (i.e., they, are intended to be discarded after a single use and may be recycled, composted or otherwise discarded in an environmentally compatible manner).

"Disposed" means the relative position of an element relative to another element.

"Fold line" means the portion of an article about which the article is bifolded to form a leading end portion and a trailing end portion. The fold line typically extends from one longitudinal edge to the other longitudinal edge in the lateral direction. In certain embodiments, the fold line may correspond to the lateral centerline of the article.

"Holding an article to the surface of a roll" means employing a holding force to one or more portions of an article in order to join the article at least temporarily to the surface of a roll such that the article is inhibited or, ideally, prohibited from traveling in a direction substantially orthogonal to the surface of the roll without reducing or removing the holding force and/or employing a peel-force. This definition is equally applicable to conveyers, e.g., the bifold conveyor assembly described hereinbelow.

"Joined" means configurations whereby an element is directly secured to another element by affixing the element directly to the other element and to configurations whereby an element is indirectly secured to another element by affixing the element to intermediate member(s) which in turn are affixed to the other element. A nonlimiting example of directly joined would be a first element pressure bonded to a second element. A nonlimiting example of indirectly joined would be a first element joined to a second element by an intermediate layer of adhesive.

"Leading end portion" means that portion of a bifolded article that is forward of the fold line in the machine direction.

"Longitudinal" means a direction running substantially perpendicular from a waist edge to an opposing waist edge of an absorbent article when the article is in a flat out, uncontracted state, or from a waist edge to the bottom of the crotch in a bifolded article. Directions within 45 degrees of the longitudinal direction are considered to be "longitudinal."

"Lateral" refers to a direction running from a longitudinal edge to an opposing longitudinal edge of an article and generally at a right angle to the longitudinal direction. Directions within 45 degrees of the lateral direction are considered to be "lateral."

"Machine direction" (also "MD" or "length direction") means the direction that is parallel to the direction of travel of an article or article element as it is processed in the forming apparatus. In a bifold process, it may be possible to have more than one machine direction when an article is undergoing simultaneous processes. In other words, a manufacturing line may have an overall machine direction, but an article may travel in directions other than the overall machine direction as it passes through various process along the manufacturing line. For example, an article having a trailing end portion and a leading end portion, each portion being attached to the surface of a different roll, may travel in two different directions simultaneously. In this example, both directions of travel may be considered the machine direction. The "cross machine direction" or "cross direction" (also "CD" or "width direction") refers to the direction perpendicular to the machine direction and in the plane generally defined by the article or article element.

"Mechanically coupled" means two or more components that, directly or indirectly, act cooperatively to form a mechanism. For example, an electric motor that drives the motion of a gate is said to be mechanically coupled to the gate. The mechanism of operation that mechanically couples the component may be any one of a number of commonly known couplers, including but not limited to: having a shaft extending between the components; a universal joint; a transmission; a linkage; a sprocket and chain; a gear head on one of the components; a gear box; a belt and pulley combination; a clutch mechanism; a spring member; a slider; a pivot; or other known forms of coupling two elements may also be considered mechanical coupling.

"Mechanically secured" means holding an object in place by a mechanical means. For example, a web of material or an absorbent article held to the outer surface of a roll with clips is considered to be mechanically secured. Conversely, holding a web of material or an absorbent article to the surface of a roll with vacuum pressure or centrifugal force is not an example of being mechanically secured.

"Peel force" means the force applied to an object in a direction that is substantially perpendicular to the plane of the surface in which the object lies or on which the object rests. A force applied in a direction within 45° of the perpendicular direction may be considered a peel force.

"Point of Tangency" means a point between the surfaces of the folding drum and the peel-roll where a first straight line, which is extended between the axes of rotation (i.e., parallel to the axes of rotation) of the folding drum and the peel-roll where the distance between their outer surfaces is at a minimum, intersects a second straight line, which is orthogonal to the first line and between the surfaces of the folding drum and the peel-roll. When the diameter of a roll or drum varies along its axis of rotation, the portion of the roll or drum having the largest diameter is used to determine the point of tangency.

"Shear force" means the force applied to an object in a direction that is substantially parallel to the plane of the surface in which the object lies or on which the object rests. A force applied in a direction within 45° of the parallel direction may be considered a shear force.

"Trailing end portion" refers to that portion of a bifolded article that is after the fold line in the machine direction.

"Training pant(s)" or "pant(s)" mean disposable absorbent articles typically having a pre-formed waist opening and leg openings. The pre-formed waist opening in typically configured to provide a fixed, closed configuration around the waist of the wearer and is intended to be put on the wearer by pulling the article over the legs of the wearer. Suitable examples of pants are described in U.S. Pat. No. 6,120,487.

"Vacuum" and "vacuum pressure" mean a pressure of less than 13000 Newtons per square meter.

For ease of understanding, portions of the following description may be exemplified in terms of an absorbent article. However, it is to be understood that while one or more particular examples recited herein may refer to a diaper or training pant, the present disclosure is not limited to such articles. The disclosed bifold and article made thereby may, in fact, be practiced to great advantage in any situation where a process or an article exhibiting the following described characteristics is required. In certain embodiments, the method and article described herein may be practiced with the apparatus U.S. non-provisional patent application entitled "System For Bifolding An Absorbent Article" filed Sep. 2, 2008 by Jay Burns, et al., and further identified by attorney docket number 10896M2.

FIG. 1 shows a partial cut-away view of a diaper 20. The diaper 20 shown in FIG. 1 is in a flat-out, uncontracted state (e.g., with no elastic induced contraction). The diaper 20 may include a liquid pervious topsheet 22; a liquid impervious backsheet 24 joined with the topsheet 22; an absorbent core 26 positioned between the topsheet 22 and the backsheet 24; side panels 28; and leg cuffs 32. The diaper 20 may further include an outer surface 52 opposed to the inner surface 50, a first waist region 36, a second waist region 38 opposed to the first waist region 36, and a crotch region 37 positioned between the first waist region 36 and the second waist region 38. The diaper 20 may also include longitudinal edges 54, a first end edge 56A corresponding to the first waist region 36, and an opposing second end edge 56B corresponding to the second waist region 38. The diaper 20 may include a longitudinal centerline 10 (e.g., positioned midway between the longitudinal side edges 54) and a lateral centerline 86 (e.g., positioned midway between opposing end edges 56A and 56B) orthogonal thereto. The end edges 56A and 56B may be substantially equal in width, as measured from opposing longitudinal side edges 54 to the longitudinal centerline 10, or length, as measured from opposing end edges 56A and 56B to the lateral centerline 86, in order to facilitate bifolding of the diaper 20, but need not necessarily be so. The diaper 20 may be bifolded along the lateral centerline 86 such that the first waist region 36 and the second waist region 38 are configured in a face-to-face relationship along the inner surface 50. A bifolded diaper according to certain embodiments may have the first end edge 56A and the second end edge 56B aligned. A bifolded diaper according to certain embodiments may have the longitudinal side edges 54 partially or entirely aligned (e.g., the longitudinal side edges 54 may be aligned only in those areas that are visible to a consumer and/or are to be permanently joined together).

Figure 2:
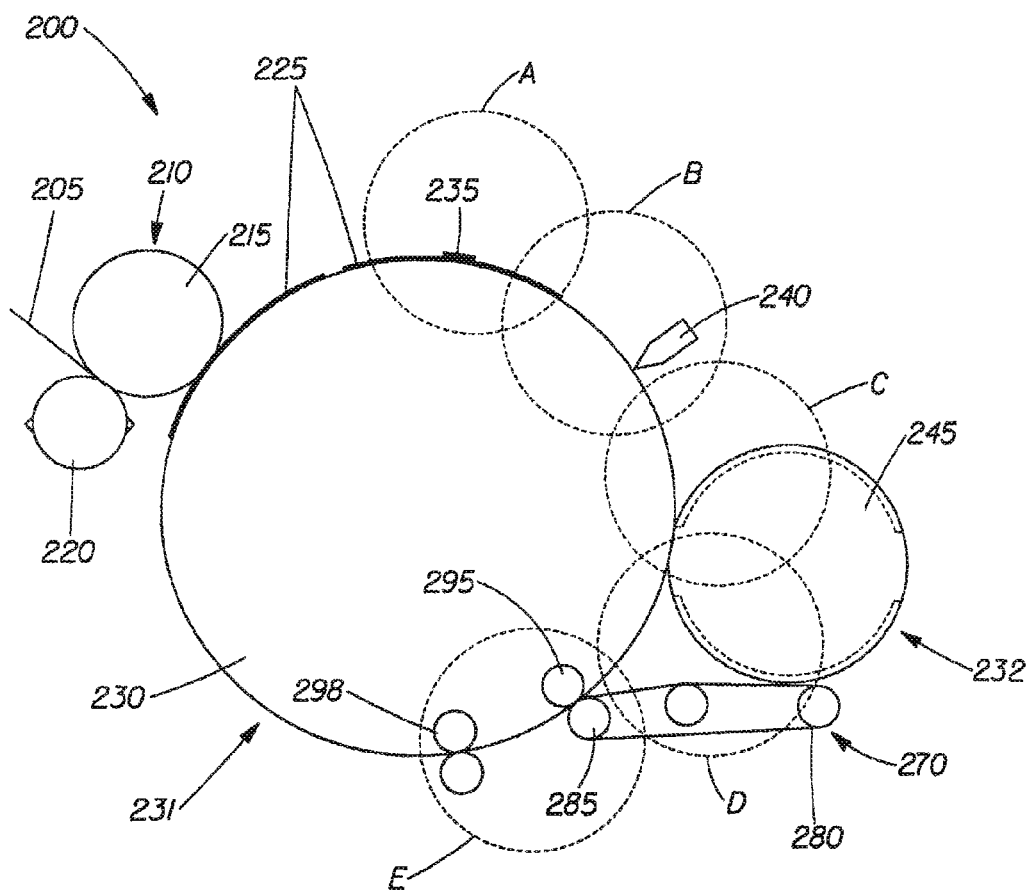
FIG. 2 is a simplified front view of an embodiment.
Figure 3:
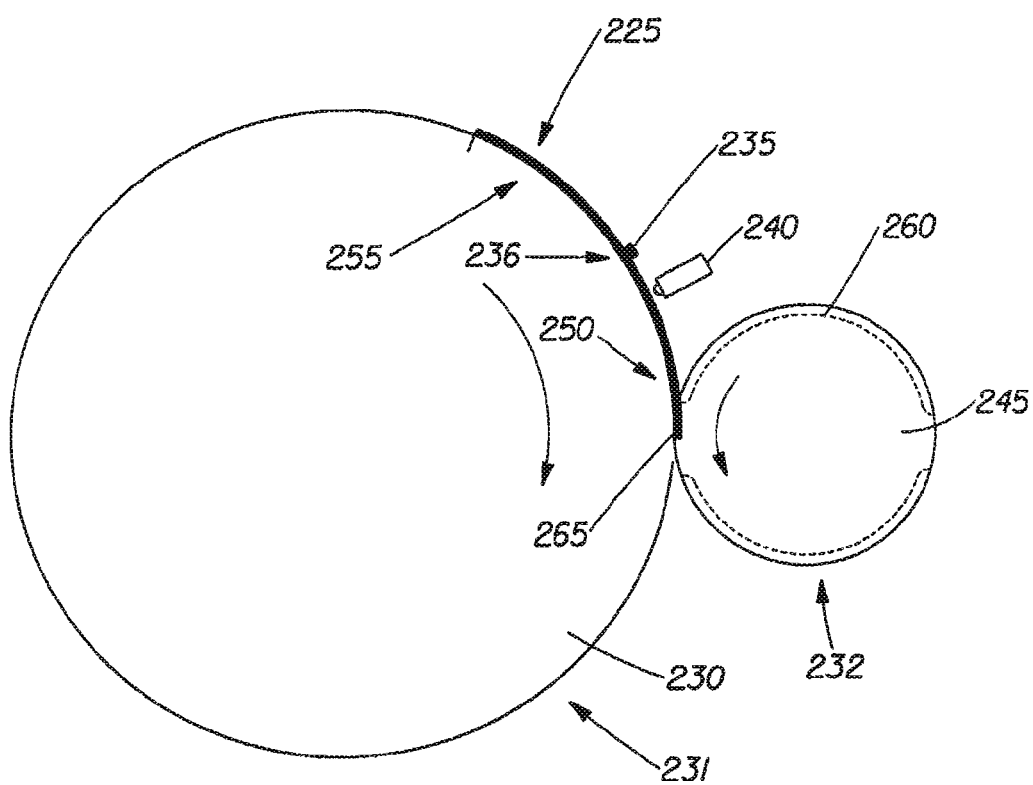
FIGS. 3-5 are simplified front views of an article progressing through a folding drum and a peel-roll.

FIG. 2 shows an example of a bifold assembly system 200 which may be suitable for bifolding an article according to the present method. In certain embodiments, the absorbent article 225 being processed by the bifold assembly system 200 may be the diaper 20 shown in FIG. 1. The present bifold method will generally be described with respect to a single article 225, but it is to be understood that the method is suitable for processing a high volume of articles. In certain embodiments, the bifold method may be used to fold 800 articles per minute, 1000 articles per minute or any suitable number of articles per minute, as desired. Where the article to be bifolded is an absorbent article 225, the absorbent article 225 may be conveyed and placed onto a rotating folding drum 230. In certain embodiments, a web of uncontracted absorbent articles 205 may be conveyed to the folding drum 230 first, and then sheared into separate absorbent articles 225, for example, by knife roll 220 and the anvil roll 215 that make up cutting member 210. In certain embodiments, absorbent articles 225 may be pre-cut, for example into absorbent articles having a length of 480 mm, and introduced into the bifold process as discrete articles 225. The folding drum 230 may be a vacuum drum that rotates in the clockwise direction, as shown in FIG. 3, at a constant or variable speed. Suitable examples of vacuum drums can be found in U.S. Pat. Nos. 5,904,802 and 6,513,221. The rotation speed of the folding drum 230 may be set to any suitable speed or speeds depending on the desired line speed. The folding drum may be a 5-up drum, i.e., being capable of fitting five articles at once. Other size folding drums may be suitable depending on the dimensions of the article being folded. Thus, for a 5-up drum, each cycle includes folding one article, and for each cycle the folding drum may rotate between 70° and 74°, ideally the drum rotates 72° for each cycle. In certain embodiments, the drum may be a 3-up drum, i.e., capable of fitting three article at once, and may rotate between 118° and 122° for each cycle (ideally 120°. It is to be understood that the drum may be configured to accommodate any number of absorbent articles, as desired. The absorbent article 225 may be transferred to the surface 231 of the folding drum 230 such that the topsheet of the article 225 is facing outward and the backsheet of the article 225 is held against the surface 231 of the folding drum 230. The absorbent article 225 is typically oriented in relation to a predetermined path such that a leading end portion 250 of the absorbent article 225 is downstream of a trailing end portion 255 of the absorbent article 225 (i.e., the leading end portion 250 enters a particular manufacturing process or sequence of processes before the trailing end portion 255). The width of the folding drum 230 may be narrower than width of the article and/or one or more article components, and a portion of the absorbent article 225 may even hang over one or more edges of the folding drum 230. In one nonlimiting example, a portion of the side panel of a diaper may hang over from 12 mm to 15 mm. Throughout the folding process, the bifold assembly system 200 may control the positioning and movement of the absorbent article 225 such that particular portions of the absorbent article 225 do not interfere with or disrupt the bifold processing performed on the absorbent article 225. The folding drum 230 may provide a holding force such as, for example, a vacuum force to hold the absorbent article 225 in a substantially flat, uncontracted state along the surface 231 of the folding drum 230 until after the absorbent article 225 is folded and/or assembled.

Figure 2B:
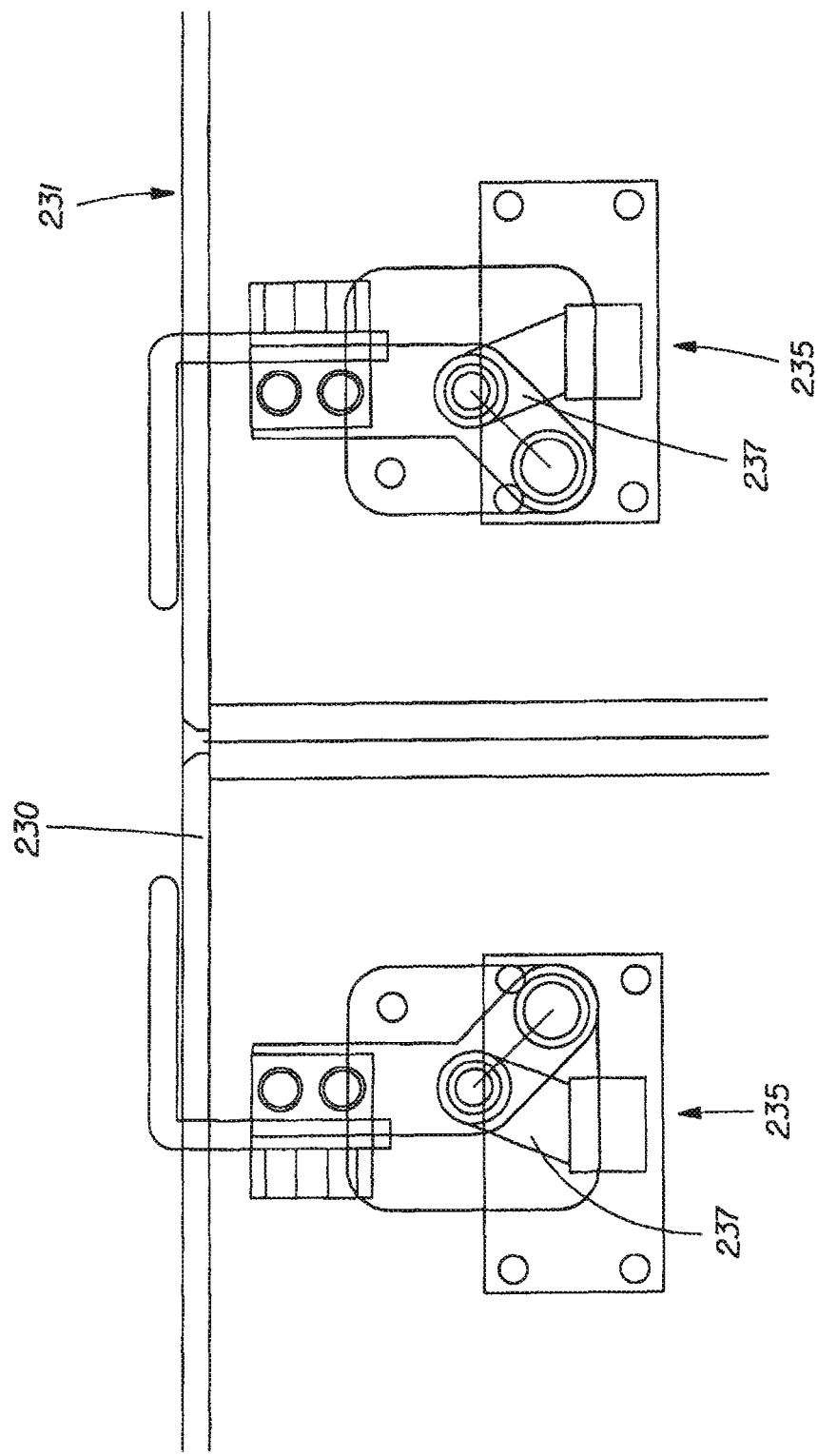

As the absorbent article 225 rotates around the folding drum 230, the article 225 may be exposed to a variety of processes. The dashed circles A-E shown in FIG. 2 identify the general location where the various processes may be performed. At location A, the article 225 may be secured to the folding drum 230 with a securing force, for example, a mechanical force provided by movable bifold clamps 235 or other mechanical securing system. The folding drum 230 may include at least one set of movable bifold clamps 235, shown in more detail in FIGS. 2A and 2B. The bifold clamps 235 may be controlled and driven by one or more cams 237 from an open position, as shown in FIG. 2A, to a closed position, as shown in FIG. 2B. The bifold clamps 235 may pivot inward from the sides of the folding drum 230 and secure the article 225 to the surface 231 of the folding drum 230 at a particular position, for example, at or near the longitudinal centerline of the article 225 along at least a portion of the longitudinal side edges. By way of example only, the diaper 20 shown in FIG. 1 may be secured to the outer surface of the folding drum 230 by the bifold clamps 235 near the lateral centerline 86 of the diaper 20 along at least of portion of the longitudinal side edges 54. The bifold clamps 235 may continue to secure the article 225 to the surface of the folding drum 230 at or near a particular portion of the absorbent article 225 until after the article 225 is folded. An example of a clamping system may be found in U.S. Pat. No. 7,399,266, issued to Aiolfi, et al., Jul. 15, 2008. It is to be understood that embodiments wherein the securing force is provided by one or more vacuum forces, electrostatic forces, and/or magnetic forces working alone or in combination with each other or the bifold clamps 235 are also contemplated herein.

The folding drum 230 may transport the article 225 to an adhesive applicator 240 at location B where an adhesive may optionally be applied. The rotating folding drum 230 may transport the article 225 toward a peel-roll 245. The peel-roll may be configured as a vacuum roll. The folding drum 230 and the peel-roll 245 may be positioned such that folding drum surface 231 is adjacent the peel-roll surface 232 at one or more locations. The folding drum 230 and the peel-roll 245 may be configured to rotate in opposite directions about axes that are parallel to each other. The minimum distance between the folding drum surface 231 and the peel-roll surface 232 may be selected to permit an article 225 to pass between the surfaces 231, 232 with little or no resistance. For example, at location C, the leading end portion 250 of the article 225 may come into contact with the peel-roll surface 231 without the progress of the article 225 being substantially impeded. The peel-roll 245 may rotate at a constant speed such that the peel-roll 245 and the folding drum 230 have similar or the same surface speed, e.g., within 0.5%, 0.2%, 0.1%, or even identical. While the bifold assembly system 200 may operate satisfactorily for a time when the speeds of the folding drum 230 and the peel-roll 245 are more than 0.5% different, the bifold process may steadily degrade resulting in undesirable misaligned article edges. Additionally or alternatively, the folding drum 230 and/or peel-roll may rotate at variable speeds. In one example of an embodiment, the article 225 may have a length of 480 mm and the peel-roll 245 may be 2-up, i.e., being capable of processing two articles 225 in one complete revolution (i.e., 360 degrees of rotation). In this embodiment, each cycle includes bifolding one article 225, and for each cycle the peel-roll 245, ideally, rotates 180°. Other size rolls with variable or constant speeds may be suitable depending on the dimensions of the article 225 being folded and the needs of the article manufacturer.

FIG. 3 shows the article 225 as it approaches the peel-roll 245. Typically, the first portion of the article 225 to arrive at peel-roll 245 is the leading end portion 250. The peel-roll 245 may provide a suitable peel-force (e.g., vacuum pressure/suction) to attract and hold at least part of the leading end portion 250 when the leading end portion 250 is, e.g., at or in the vicinity of the point of tangency 265. In one example of an embodiment, the peel-force exerted by the peel-roll 245 may pull at least a portion of the leading end portion 250 of the article 225 away from the folding drum 230. As the leading end portion 250 of the article 225 is pulled away from the folding drum 230, any force exerted by the folding drum 230 on the leading end portion 250 of the article 225 may be simultaneously or sequentially removed or reduced. The peel-roll 245 may include a continuous recessed pocket 260 about its perimeter to facilitate vacuum catching articles that have portions of greater thickness than other portions of the article. In the example of a disposable diaper, the area(s) of the diaper corresponding to the absorbent core is typically thicker than the area(s) that does not include the absorbent core. Therefore, in order to provide suitable clearances between the peel-roll 245 and the folding drum 230 (e.g., bring them closer together) it may be desirable to configure the recessed pocket 260 of the peel-roll 245 to hold the absorbent core area of the diaper. Other suitable peel-roll 245 configurations contemplated herein include a peel-roll 245 comprising: a single recessed pocket 260 around only a portion of the peel-roll 245; a plurality of recessed pockets 260 intermittently spaced around the peel-roll 245; or no recessed pocket 260.

Figure 5:
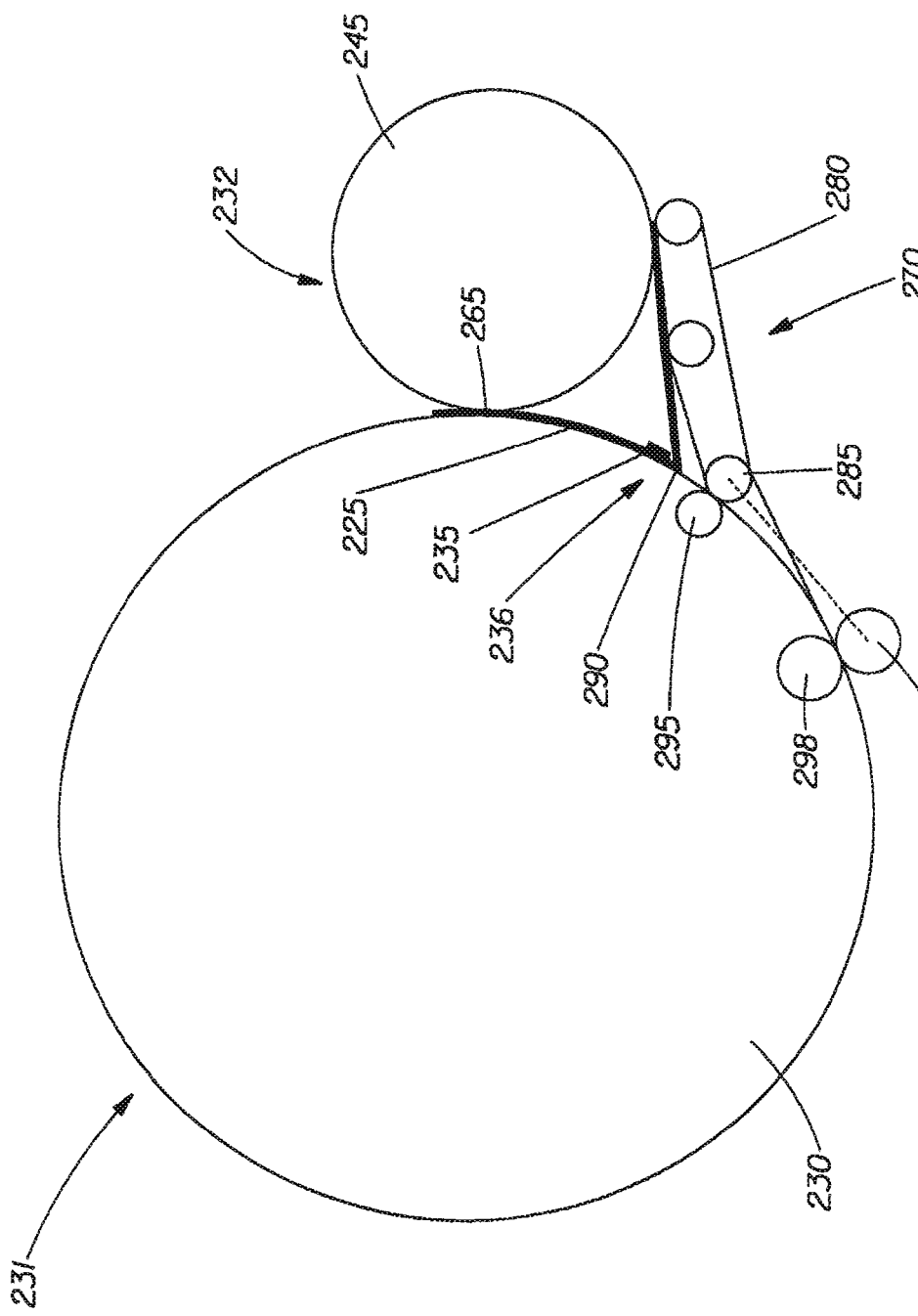

At location D, the article 225 may begin to wrap around the peel-roll 245 up to the portion of the article 225 secured by the bifold clamps 235 and at least some portion(s) adjacent thereto. The portion of the article 225 secured by the bifold clamps 235 may correspond approximately to the lateral centerline of the article 225, as shown in FIG. 5. As a larger portion of the article 225 is transferred to the peel-roll 245, the holding force exerted by the folding drum 230 on the article 225 or portions of the article 225 may be reduced or removed accordingly. In embodiments comprising movable bifold clamps 235, the bifold clamps 235 typically remain in the closed position, thereby permitting the article 225 to only be transitioned to the peel-roll 245 up to the portion of the article secured by bifold clamps 235 ("clamped portion" 236). The remaining portion of the article 225, i.e., the trailing end portion 255 may be held against the folding drum surface 231 by the holding force and/or securing force, for example, vacuum force and/or bifold clamps 235.

As the folding drum 230 continues to rotate, the bifold clamps 235 and the clamped portion 236 continue to move with the folding drum surface 231. When the bifold clamps 235 reach a particular point in the process, they may exert a force such as, for example, a shear force on the leading end portion 250. The shear force felt by the leading end portion 250 may be in a direction that is substantially different from or even opposite the direction of rotation of the peel-roll 245. Thus, the leading end portion 250 may begin to slow down or even stop moving along with the peel-roll surface 232. The leading end portion 250 may experience slippage on the peel-roll 245 (i.e., the peel roll 245 continues to rotate while the position of the leading end portion remains constant or even begins moving towards the folding drum 230), and as the folding drum 230 continues to rotate the leading end portion 250 may eventually separate from the surface of the peel-roll 232.

Figure 4:
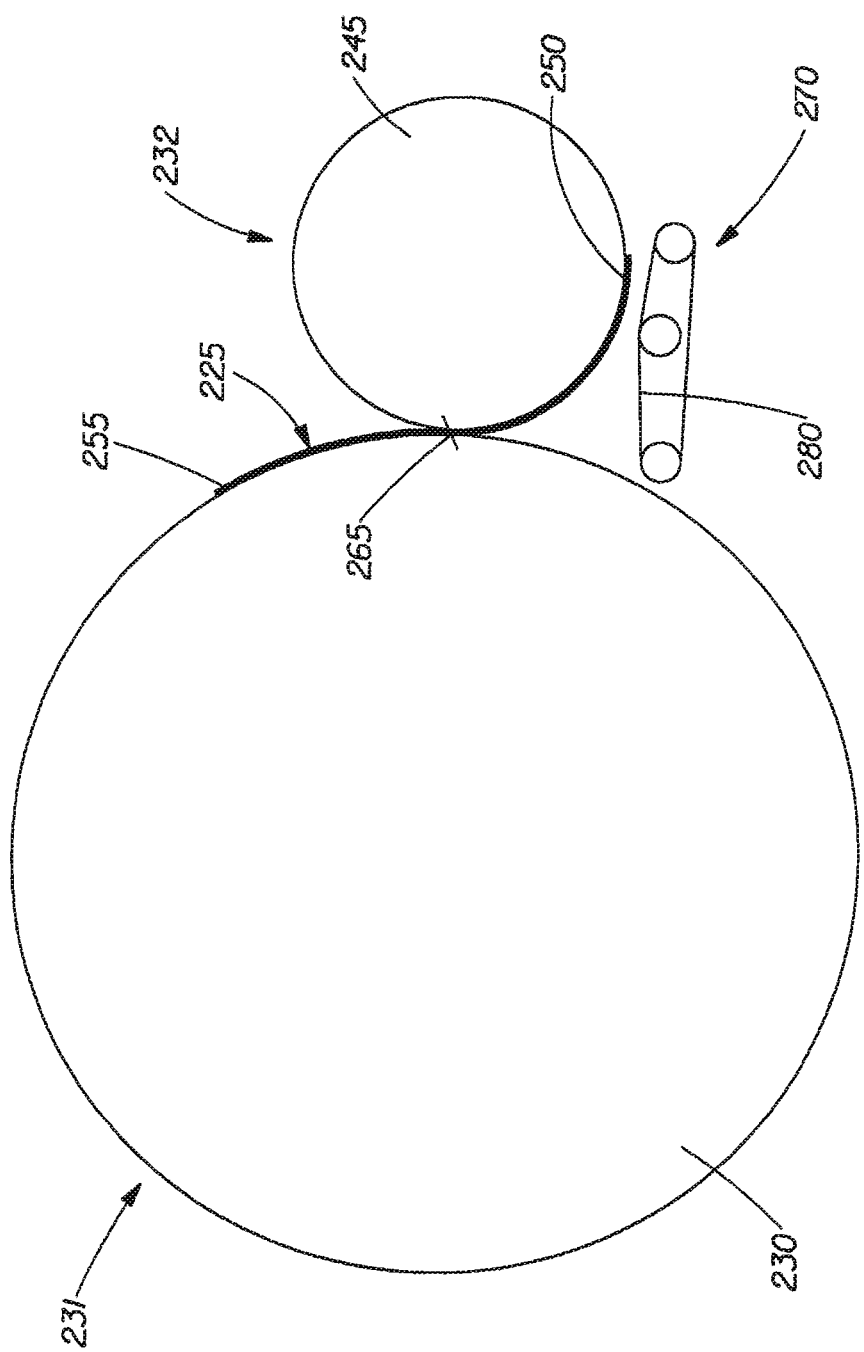

FIGS. 2, 4, and 5 show examples of an embodiment of a bifold assembly system 200 that includes a bifold conveyer assembly 270. Configuring the bifold conveyer assembly 270 to act cooperatively with the folding drum 230 and the peel-roll 245, as described hereinbelow, may provide a suitably aligned bifolded article. In order to configure the bifold conveyor assembly 270 to act cooperatively with the folding drum 230 and the peel-roll 245, it may be desirable to provide a variable speed vacuum conveyor 280 surface for engaging the leading end portion 250. By "engaging" it is generally meant coming into close proximity (e.g., <10 cm, up to and including physically contacting the absorbent article 225) such that the suction present at the surface of the vacuum conveyor 280 can be suitably applied to the absorbent article 225. In certain embodiments, the vacuum conveyor 280 may include a movable foraminous conveyor belt configured in an endless loop. In certain embodiments, the vacuum conveyor 280 may be in the form of a vacuum roll. It may be desirable to slow or even temporarily stop the surface of the vacuum conveyor 280 from moving prior to, while, and/or after engaging the leading end portion 250. In certain embodiments, the surface of the vacuum conveyor 280 and the leading end portion 250 may be moving in substantially the same direction (i.e., toward the folding drum 230). As the leading end portion 250 is separated from the peel-roll surface 232, at least partially due to the shear force exerted by the bifold clamps 235, the bifold clamps 235 will typically continue to pull the leading end portion 250 toward the folding drum 230 as the folding drum 230 rotates. Therefore, the surface of the vacuum conveyor 280 may be configured to move at a relatively slow speed in the same direction as the leading end portion 250 is moving (i.e., toward the folding drum 230), and the relative speed between the leading end portion 250 and the surface of the vacuum conveyor 280 during engagement may be reduced along with the undesirable effects typically associated with a higher relative speed engagement. In certain embodiments, the vacuum conveyor 280 may engage the leading end portion 250 when the leading end portion 250 is still held to the peel-roll surface 232. In such an embodiment, it may be desirable to completely stop the surface of the vacuum conveyor 280 prior to engaging the leading end portion 250.

Upon engaging the leading end portion 250, the bifold conveyer assembly 270 may be configured to apply vacuum pressure to the leading end portion 250. It may be desirable to configure the suction exerted by the bifold conveyer assembly 270 to be strong enough to overcome the peel-force exerted by the peel-roll 245. In certain embodiments, it may be desirable to reduce or remove the peel-force exerted by the peel-roll 245 when the absorbent article 225 reaches a desired position or when the vacuum conveyor 280 engages the leading end portion 250. For example, the suction exerted by the peel-roll 245 may be reduced or removed when the clamped portion 236 reaches the point of tangency 265 or after the clamped portion 236 passes through the point of tangency 265. In certain embodiments, the vacuum conveyor 280 may engage the leading end portion 250 when the leading end portion 250 begins to experience slippage due to the force exerted on the leading end portion 250 by the clamps 235. In certain embodiments, the vacuum conveyor 280 may engage the leading end portion 250 when the leading end portion 250 is traveling in substantially the same direction as the vacuum conveyor 280 (e.g., after the leading end portion separates from the peel-roll surface 232). In certain embodiments, the moving surface of the vacuum conveyor 280 may be accelerated after engaging the leading end portion 250 to match the surface speed of the folding drum 230. In this way, the leading end portion 250 and the trailing end portion 255 may be traveling at substantially the same speed when the two portions 250, 255 are brought together in a face-to-face relationship. However, embodiments where the surface of the vacuum conveyor 280 is accelerated during or even prior to engaging the leading portion 250 are also contemplated herein.

In some instances, at least a portion of the surface of the vacuum conveyor 280 may be traveling in substantially the opposite direction as the peel-roll 245, and consequently any premature engagement of the vacuum conveyor apparatus 280 with the leading end portion 250 such as, for example, before the leading end portion 250 separates from the peel-roll surface 232 may undesirably impact the bifold process. In order to minimize or even eliminate the possibility of premature engagement of the vacuum conveyor 280 with the leading end portion 250, it may be desirable to maintain a suitable distance or gap between the peel-roll surface 232 and the surface of the vacuum conveyor 280 when the vacuum conveyor 280 is not engaging or attempting to engage the leading end portion 250. In certain embodiments, the surface of the vacuum conveyor 280 may be positioned relative to the peel-roll 245 and/or folding drum 230 by a positioning mechanism mechanically coupled to the bifold conveyor assembly and/or the vacuum conveyor 280. Suitable examples of positioning mechanisms include one or more cams, pistons, gears, pulleys, and the like. The positioning mechanism may be configured to automatically vary the distance between the surface of the vacuum conveyor 280 and the surface of the peel-roll 245 in a continuous or intermittent fashion. In certain embodiments, the distance between the folding drum surface 231 and the surface of the vacuum conveyor 280 may be held constant or varied, as desired. In certain embodiments, the vacuum conveyor 280 may pause at a particular position during the bifold process, for example, at the "top of the upstroke" (i.e., when the distance between the vacuum conveyor 280 and the peel-roll 245 is at a minimum), the "bottom of the downstroke" (i.e., when the distance between the vacuum conveyor 280 and the peel-roll 245 is at a maximum), and/or upon engaging the leading end portion 250. The positioning mechanism may have any suitable stroke length, for example, a stroke length of greater than 1 mm, between 1 mm and 20 cm, 1 mm and 20 mm, 1 mm and 10 mm, or even 1 mm and 5 mm. The positioning mechanism may be configured to suitably position the vacuum conveyor 280 for engaging the leading end portion 250 during the "upstroke" (i.e., when the vacuum conveyor 280 is being brought closer to the peel-roll 245) and to provide a suitable gap between the vacuum conveyor 280 and the peel-roll 245 during the "downstroke" (i.e., when the vacuum conveyor 280 is moved further from the peel-roll 245). In certain embodiments, the positioning mechanism may be configured such that the leading end portion 250 is transferred to the vacuum conveyor 280 at the top of the upstroke. Additionally or alternatively, it may be desirable to vary the position of the peel-roll surface 232 relative to the vacuum conveyor 280. Suitable gap distances are typically at least greater than the thickness of the absorbent article 225, for example, greater than 1 mm, between 1 mm and 20 cm, or even between 1 mm and 20 mm. One particularly suitable method of providing a gap may include a bifold conveyer assembly 270 that includes a cam with a 3 mm stroke length for continuously varying the position of the vacuum conveyor 280 surface relative to the peel-roll surface 232.

Folding processes that do not include a bifold conveyor assembly 270 and/or a vacuum conveyor 280 may not be capable of controllably handling the leading end portion 250 in order to provide a bifolded disposable absorbent article 225 having aligned end edges. Ideally, the leading end portion 250 is removed from the peel-roll 245 and held on the vacuum conveyor 280 such that the side edges and end edges of the absorbent article 225 are aligned when the leading end portion 250 and the trailing end portion 255 are brought into a face-to-face configuration by the bifold assembly system 200. By providing a bifold conveyer assembly 270 that is capable of applying a peel-force to the leading end portion 250 at the peel-roll surface 232, the uncertainty as to how the leading end portion 250 will be oriented when it is released from the peel-roll 245 may be reduced. When the leading end portion 250 is held and transported by a variable speed and/or variable position vacuum conveyor 280, the amount of control that can be exercised over the orientation of the leading end portion 250 may also increase. Therefore, the ability of an operator of the bifold assembly system 200 to align the side edges and/or end edges of the absorbent article 225 may increase.

At location E in FIG. 2, the new leading end portion 290 of the folded article may optionally enter the glue compression rolls 295, where components of the absorbent article 225 may be adhesively joined to themselves or other components, as desired. The article may then be transported to a pair of compression rolls 298 to reinforce the optional adhesive bond(s) with high-pressure bonding. The processes at location E may be suitably configured for forming the bifolded article 225 into, e.g., a training pant product.

Figure 6:
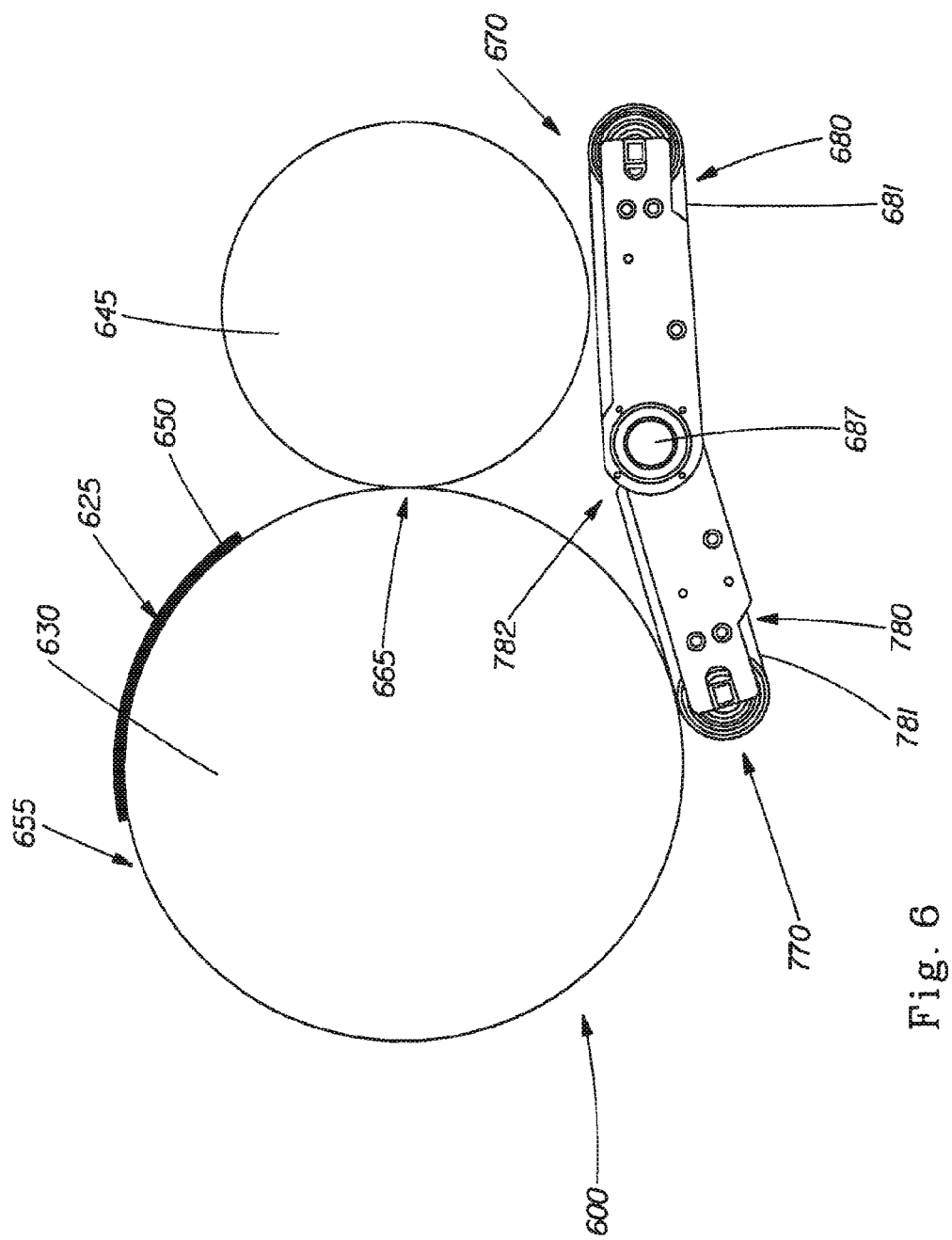
FIG. 6 is a front view of a two-conveyor bifold apparatus.

FIG. 6 shows an example of a bifold assembly system 600 with first and second bifold conveyor assemblies 670 and 770. The bifold assembly system 600 shown in FIG. 6 may be configured to operate in substantially the same manner as the single-conveyor bifold assembly system 200 described above, with the exception of the process(es) described at location D. In this example, the first bifold conveyor assembly 670 includes a first vacuum conveyor 680 for engaging the leading end portion 650 of an article 625 and transferring the leading end portion 650 to the second vacuum conveyor 780 of the second bifold conveyor assembly 770. The first and second vacuum conveyors 680 and 780 may each include one or more discrete movable surfaces such as, for example, one or more belts configured in an endless loop and driven by a drive mechanism. The first and second vacuum conveyors 680 and 780 may be configured to provide suitable vacuum pressure to receive, hold, and/or transfer the leading end portion 650. It may be desirable to vary the position of the first vacuum conveyor 680 surface relative to the peel roll 645, for example, by including a positioning mechanism similar to that described above in bifold assembly system 200. The second position of the second vacuum conveyor 780 surface may be fixed relative to the surface of the folding drum 630, but need not necessarily be so. In certain embodiments, the first vacuum conveyor 680 may be configured to engage the leading end portion 650 at a suitable time and/or when the leading end portion 650 is in a suitable position, for example, at the top of the upstroke of the vacuum conveyor 680 or when the leading end portion 650 reaches the point of tangency 665, and then transport the leading end portion 650 toward the receiving end 782 of the second vacuum conveyor 780. It may be desirable to configure the first vacuum conveyor 680 to engage the leading end portion 650 when the surface speed of the first conveyor belt 681 is relatively slow, or even when the conveyor belt 681 is not moving at all, in order to decrease the risk of damaging the article 625. In addition, it is believed, without being limited by theory, that engaging the leading end portion 650 with a slow moving or stopped vacuum conveyor surface may at least partially reduce process variation (e.g., misalignment of two diaper edges), due to product and/or raw material variation. After receiving the leading end portion 650, the belt speed of the first conveyor 680 may be increased to substantially match the belt speed of the second conveyor 780. The leading end portion 650 is carried toward and ultimately transferred to the second vacuum conveyor 780 by the first vacuum conveyor 680. The first and second bifold conveyor assemblies 670 and 770 may be configured to share one or more common elements such as, for example, a shaft 687. Shaft 687 may be coupled to, e.g., a variable speed drive motor and configured to drive the endless belt 681 of the first vacuum conveyor 680 at one or more speeds. The shaft 687 may also include one or more free-spinning rollers or pulley-like elements that enable the shaft 687 to simultaneously operate as an idler roll for the endless belt 781 of the second vacuum conveyor 780. The second vacuum conveyor 780 may be driven by, e.g., a constant speed motor that drives the second vacuum conveyor belt 781 at, e.g., the surface speed of the folding drum 630, by way of a mechanical coupling. By sharing shaft 687, the first and second vacuum conveyor belts 681, 781 may be configured to overlap at one end in the machine direction (see FIG. 7), and thereby facilitate transfer of the leading end portion 650 from the first vacuum conveyor 680 to the second vacuum conveyor 780. During transfer of the leading end portion 650 from the first vacuum conveyor 680 to the second vacuum conveyor 780, the vacuum pressures on the first and second conveyors 680, 780 may be configured (e.g., decreased/increased and/or stopped/started) to facilitate transfer of the leading end portion 650. After receiving the leading end portion 650, the second vacuum conveyor 780 transports the leading end portion 650 toward the folding drum 630 at a constant speed (e.g., the surface speed of the folding drum 630) until the leading end portion 650 and the trailing end portion 655 of the article 625 are aligned in a bifolded configuration.

Figure 7:
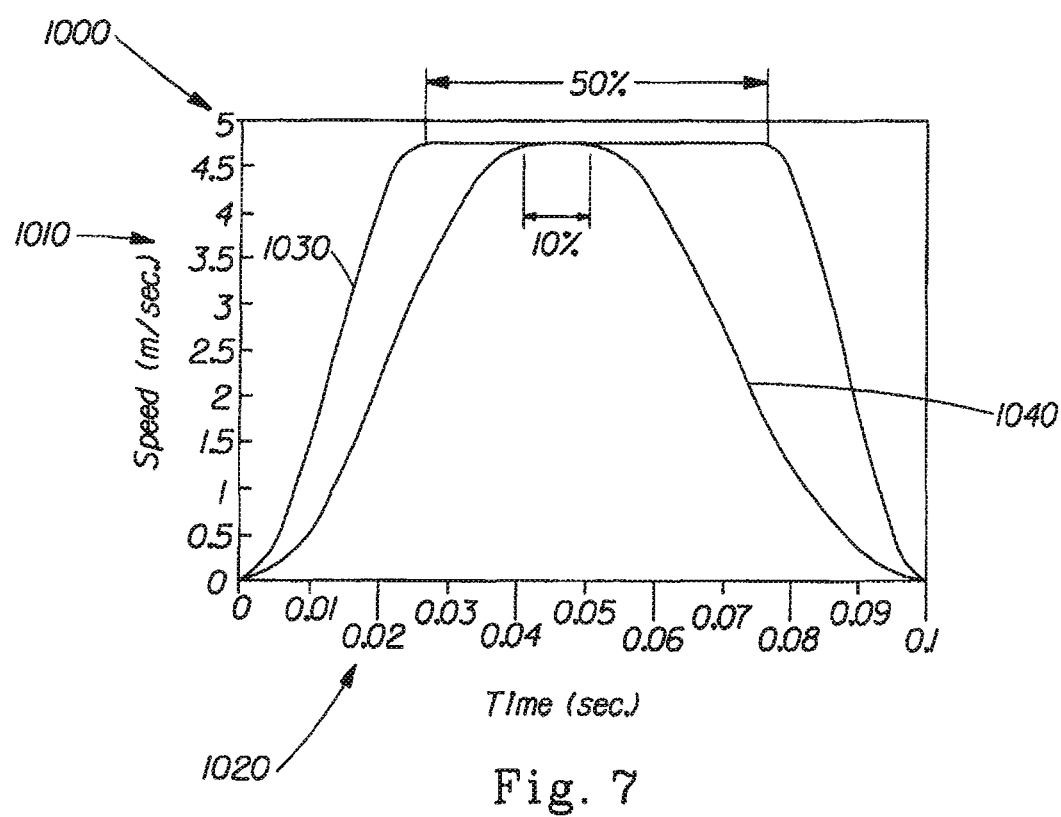
FIG. 7 is a graphical depiction of a time versus speed relationship.

FIG. 7 shows a graphical illustration 1000 of an example of speed/time relationship for a single-conveyor bifold assembly 1030 and a two-conveyor bifold assembly 1040. The x-axis 1020 of the graph represents the amount of time that the bifold conveyor is operating at a particular speed. The y-axis 1010 shows the speed at which the bifold conveyor is operating. In the case of the two-conveyor system 1040, the graph 1000 shows the speed/time relationship for the first conveyor (i.e., the conveyor that engages the leading end portion of an article on the peel-roll and transports the leading end portion to the second conveyor). As can be seen from the graph, a two-conveyor system 1040 may provide more time for the first conveyor to speed up and slow down between the relatively high surface speed of a folding drum and the relatively low speed of engagement (i.e., the speed of the conveyor when it engages the leading end portion of an article) than the single conveyor system 1030. The increased amount of time for increasing and decreasing the speed of the conveyor may result in higher manufacturing line speed capability. In certain embodiments, a servo motor may be used to position the conveyor surfaces, and in such embodiments the two-conveyor system may reduce the position error of the servo (at least in part due to the potential lower load on the servo) as well as potentially reduce servo costs due to the lower precision requirements of the servo. Further, the increased amount of time for increasing and decreasing the speed of the conveyor may result in less wear and tear on the bifold conveyor assembly, the vacuum conveyor, the article, and/or components of these. While particular examples may be described as including one or two vacuum conveyors, it is to be understood that embodiments comprising three or more vacuum conveyors are also contemplated herein.

In order to exemplify the advantage(s) of the disclosed bifolding process, two commercially available disposable absorbent articles were compared to a disposable absorbent article bifolded according to the disclosed process. Table 1 summarizes the test results obtained from measuring LITTLE SWIMMERS brand swimming pants, large size (i.e., for babies over 14.5 kg), available from the Kimberly-Clark Corporation, Neenah, Wis. Ten of the swimming pants were taken from the same package and measured according to the Alignment Test described in more detail below.

TABLE 1

| Kimberly Clark Little Swimmers | | | | | | | | |
|---|---|---|---|---|---|---|---|---|
| CD Left Waist | CD Left Leg | CD difference Left | CD Right Waist | CD Right Leg | CD difference Right | MD Left | MD Right | MD difference |
| 36 | 40 | 4 | 43 | 54 | 11 | −8 | 2 | 10 |
| 31 | 40 | 9 | 45 | 50 | 5 | −6 | 5 | 11 |
| 31 | 35 | 4 | 46 | 52 | 6 | −16 | 2 | 18 |
| 36 | 44 | 8 | 44 | 51 | 7 | −5 | 2 | 7 |
| 34 | 46 | 12 | 47 | 48 | 1 | −5 | 8 | 13 |
| 36 | 43 | 7 | 44 | 55 | 11 | −8 | 6 | 14 |
| 34 | 43 | 9 | 42 | 48 | 6 | −14 | −1 | 13 |
| 35 | 43 | 8 | 41 | 47 | 6 | −7 | 4 | 11 |
| 31 | 36 | 5 | 46 | 56 | 10 | −6 | 4 | 10 |
| 34 | 44 | 10 | 45 | 51 | 6 | −4 | 3 | 7 |
| Average | | 7.6 | | | 6.9 | | | 11.4 |

Table 2 summarizes the test results obtained from measuring FMV brand, medium-sized training pants, available from the Tyco International, Ltd., Hamilton, Bermuda. Ten of the training pants were taken from the same package and measured according to the Alignment Test described in more detail below.

TABLE 2

| FMV Product | | | | | | | | |
|---|---|---|---|---|---|---|---|---|
| CD Left Waist | CD Left Leg | CD difference Left | CD Right Waist | CD Right Leg | CD difference Right | MD Left | MD Right | MD difference |
| 6.5 | 10.5 | 4 | 1.5 | 6 | 4.5 | 0 | 3 | 3 |
| 4.5 | 7 | 2.5 | 2 | 7.5 | 5.5 | 2 | 6.5 | 4.5 |
| 6 | 10 | 4 | 0.5 | 4.5 | 4 | 1 | 4 | 3 |
| 6 | 7.5 | 1.5 | 4.5 | 6.5 | 2 | 1 | 4 | 3 |
| 5.5 | 8 | 2.5 | 1.5 | 6 | 4.5 | 3.5 | 1 | 2.5 |
| 7 | 8 | 1 | 3.5 | 7.5 | 4 | 3 | 6 | 3 |
| 4 | 8 | 4 | 1 | 8 | 7 | 4 | 8 | 4 |
| 6.5 | 9 | 2.5 | 4 | 9 | 5 | 1 | 4 | 3 |
| 4.5 | 10 | 5.5 | 1.5 | 8 | 6.5 | 0 | 4 | 4 |
| 4 | 8 | 4 | 2.5 | 10 | 7.5 | 0 | 5 | 5 |
| Average | | 3.15 | | | 5.05 | | | 3.5 |

Table 3 summarizes the test results obtained from measuring ten training pant samples bifolded according to the bifold process disclosed herein. The training pant samples were fed into the bifold process by hand as individual disposable absorbent articles. The samples were then measured according to the Alignment Test described in more detail below.

TABLE 3

| | Bifolded Sample | | | | | | | |
|---|---|---|---|---|---|---|---|---|
| CD Left Waist | CD Left Leg | CD difference Left | CD Right Waist | CD Right Leg | CD difference Right | MD Left | MD Right | MD difference |
| 0 | 0.6 | 0.6 | 0 | 0.6 | 0.6 | 5.1 | 5.1 | 0 |
| 5.1 | 0.6 | 4.5 | 2.5 | 5.1 | 2.6 | 3.8 | 7.6 | −3.8 |
| 2.5 | 3.8 | 1.3 | 1.3 | 3.8 | 2.5 | 6.3 | 7.6 | −1.3 |
| 3.8 | 3.2 | 0.6 | 1.3 | 2.5 | 1.2 | 7.6 | 7.6 | 0 |
| 2.5 | 7.6 | 5.1 | 1.3 | 1.9 | 0.6 | 7.6 | 6.3 | 1.3 |
| 2.5 | 0 | 2.5 | 2.5 | 0 | 2.5 | 6.3 | 7.6 | −1.3 |
| 2.5 | 5.7 | 3.2 | 1.3 | 3.2 | 1.9 | 8.9 | 7.6 | 1.3 |
| 1.3 | 3.8 | 2.5 | 1.3 | 5.1 | 3.8 | 7.6 | 6.3 | 1.3 |
| 3.8 | 7.6 | 3.8 | 3.8 | 0.6 | 3.2 | 7.6 | 10.2 | −2.6 |
| 2.5 | 7 | 4.5 | 2.5 | 3.2 | 0.7 | 10.2 | 10.2 | 0 |
| Average | | 2.86 | | | 1.96 | | | 1.29 |

TABLE 4

Results Summary:

| | Average CD Accuracy, mm | MD accuracy, mm |
|---|---|---|
| Kimberly Clark Little Swimmers | 7.25 | 11.4 |
| FMV Product | 4.10 | 3.5 |
| Bifolded Sample | 2.41 | 1.29 |

Table 4 summarizes the results from Tables 1-3, and shows the average CD accuracy and the average MD accuracy for each of the three samples. From Table 4, it can be seen that only the sample bifolded according to the presently disclosed bifolding process was aligned.

Test Method for the Alignment Test

One purpose of the Alignment Test is to determine the degree of alignment between the front and back edges of a pant that has been bifolded in the machine direction. Another purpose of the Alignment Test is to determine the alignment of the front and back waist edges of a pant when the front and back edges of the absorbent article are seamed at the side of the absorbent article.

Figure 8:
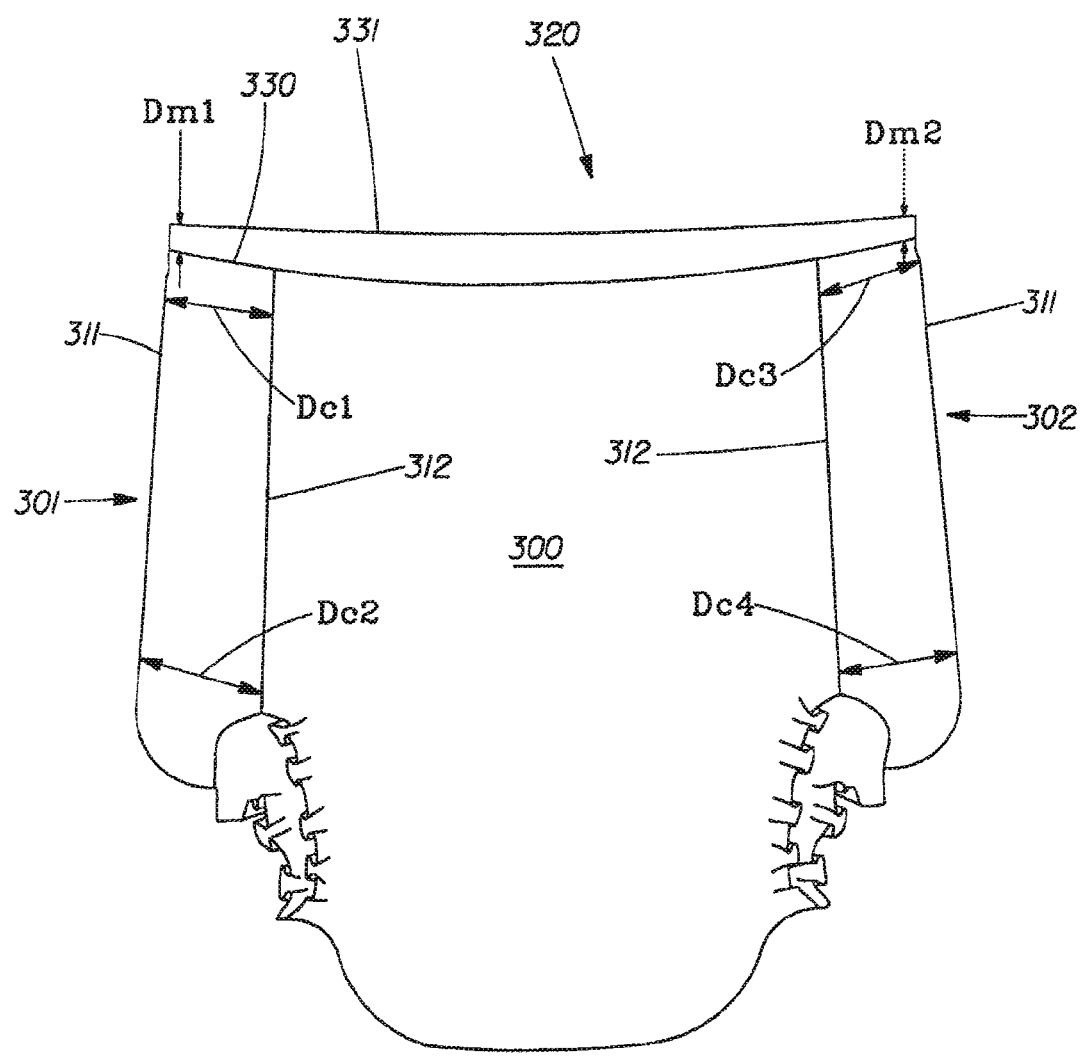
FIG. 8 is plan view of a disposable absorbent article configured for the Alignment Test.

Procedure:

FIG. 8 shows a disposable absorbent article 320 in the form of a pant. To determine the cross direction folding accuracy (i.e., how straight the front and back edges are when seamed at the pant side), first turn the pant 320 inside out so that the side that is normally comprises the outer surface of the pant 320 now comprises the inner surface. On both the left side 301 and right side 302 of the front face 300, locate the side seam line 311. Next, locate a raw material edge 312 that runs parallel to the machine direction, for example leg cuffs, elastic stretch materials, a glue bead, etc. Smooth out any wrinkles that may be present in the area between the raw material edge 312 and the side seam 311. Then, keeping the article in a substantially contracted state (i.e., do not stretch the elastic portions of the article, or any other portion), measure and record the distances from the side seam 311 to the parallel material edge 312 in millimeters (mm) at the following four locations: left side at waist $D_{c1}$; left side at leg $D_{c2}$; right side at waist $D_{c3}$; and right side at leg $D_{c4}$. Repeat the distance measurements for a total of 10 pads. Subtract the distance measured for the left side at waist $D_{c1}$ from the distance measured for the left side at leg $D_{c2}$ for each of the 10 pads and then repeat for the right side 302 (i.e. subtract right side at waist $D_{c3}$ distance from right side at leg $D_{c4}$ distance).

Record the calculated differences in waist to leg distance as absolute values for each of the left side 301 and the right side 302. Next, calculate the average difference for the left side 301 values (i.e., add the left side 301 values together and divide by 10). Repeat for the right side 302 values. This is the average CD difference for each of the left and right sides 301, 302. Next, calculate the average CD accuracy value caused by the bifolding process by adding the left and right average CD misalignment values together and dividing the sum by 2.

To determine the machine direction folding accuracy (i.e., how accurate the front end edge 330 matches up with the rear end edge 331 in the machine direction) first turn the pant 320 inside out and then place the front side 300 of the pant 320 up so that it is visible to the tester. Smooth out any wrinkles that may be present in the area adjacent the side seam 311. Keeping the article in an uncontracted state, measure and record the distances measure the left side distance $D_{m1}$ and right side distance $D_{m2}$ between the front end edge 330 and rear end edge 331 of the pant 320 at the side seam line 311. If the rear end edge 331 is protruding above the front end edge 330 (as shown in FIG. 10), record the measured distance as a positive number. If the front end edge 330 is protruding above the back end edge 331 (i.e., the back end edge is not visible when the pant 320 is substantially flat), record the measured distance as a negative number. Subtract the right side distance $D_{m2}$ from the left side $D_{m1}$ and record the absolute value of the difference as the MD difference for the pant 320 sample. Repeat the measurement and calculation for a total of 10 samples. Average the 10 MD difference values and record the result as the MD accuracy.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of the invention.

What is claimed is:

1. A method for folding an article into a bifold configuration, the method comprising:
   a. placing the article onto a folding drum surface, the disposable absorbent article having a leading end portion and a trailing end portion;
   b. holding the article to the folding drum surface with a holding force;
   c. transferring at least a portion the leading end portion of the article to a peel-roll surface positioned adjacent the folding drum surface;
   d. applying a peel-force to the leading end portion such that the leading end portion is held to the peel-roll surface by the peel-force;
   e. holding at least a portion of the trailing end portion to the folding drum surface;
   f. transferring the leading end portion from the peel-roll surface to a movable surface of a first vacuum conveyor, the movable surface of the first vacuum conveyor configured to have a first speed and a second speed, the movable surface of the first vacuum conveyor being driven by a drive mechanism coupled to the movable surface of the first vacuum conveyor, the leading end portion being transferred to the movable surface of the first vacuum conveyor when the movable surface of the first vacuum conveyor engages the leading end portion at the first speed, the movable surface of the first vacuum conveyor being configured to apply a vacuum force to the leading end portion when the movable surface of the first vacuum conveyor engages the leading end portion;
   g. holding the leading end portion from (f) to the movable surface of the first vacuum conveyor with the vacuum force;
   h. accelerating the movable surface of the first vacuum conveyor to the second speed;
   i. transferring the leading end portion from the movable surface of the first vacuum conveyor to a second vacuum conveyor, the second vacuum conveyor including a second vacuum conveyor movable surface; and
   j. transferring the leading end portion from the second vacuum conveyor movable surface to the folding drum such that the article is folded into a bifolded configuration.

2. The method of claim 1, wherein the first vacuum conveyor is coupled to a positioning mechanism, the positioning mechanism configured to position the movable surface of the first vacuum conveyor in a first position and a second position, the distance between the movable surface of the first vacuum conveyor and the peel-roll surface in the first position being less than the distance between the movable surface of the first vacuum conveyor and the surface of the peel-roll in the second position.

3. The method of claim 2, wherein the leading end portion is engaged by the movable surface of the first vacuum conveyor when the movable surface of the first vacuum conveyor is in the first position.

4. The method of claim 2, wherein the leading end portion is transferred to the movable surface of the second vacuum conveyor from the movable surface of the first vacuum conveyor when the movable surface of the first vacuum conveyor is in the second position.

5. The method of claim 2, wherein the positioning mechanism varies the position of the movable surface of the vacuum conveyor from about 1 mm to 20 cm from the peel-roll surface.

6. The method of claim 2, wherein the positioning mechanism continuously varies the position of the movable surface of the vacuum conveyor.

7. The method of claim 1, wherein the leading end portion is transferred to the movable surface of the second vacuum conveyor from the movable surface of the vacuum conveyor at the second speed.

8. The method of claim 1, wherein the leading end portion is transferred to the folding drum from the movable surface of the second vacuum conveyor at the second speed.

9. The method of claim 1, wherein the leading end portion is transferred to the folding drum from the movable surface of the second vacuum conveyor at a third speed.

10. The method of claim 1, wherein the folding drum surface has a folding drum surface speed, and the folding drum surface speed and the second speed are substantially the same.

11. The method of claim 1, wherein the first speed is zero.

12. The method of claim 1, wherein a portion of the article is secured to the folding drum with a securing force.

13. The method of claim 12, wherein the securing force is provided by movable clamps.

14. The method of claim 12, wherein the article includes first and second opposing longitudinal side edges and a lateral centerline and the securing force is applied to the lateral centerline portion of at least one of the side edges.

15. The method of claim 1, wherein the movable surface of the first vacuum conveyor engages the leading end portion while the leading end portion is held to the peel-roll surface.

16. The method of claim 1, wherein the peel-force is at least one of reduced or removed prior to engaging the leading end portion with the movable surface of the first vacuum conveyor.

17. The method of claim 1, wherein the movable surface of the second conveyor is coupled to a constant speed drive motor.

18. The method of claim 1, wherein the article is aligned when the article is bifolded.

* * * * *